US00PP18577P2

(12) United States Plant Patent
Bernuetz

(10) Patent No.: US PP18,577 P2
(45) Date of Patent: Mar. 11, 2008

(54) POINSETTIA PLANT NAMED 'BONPOIAKAICHI'

(50) Latin Name: *Euphorbia pulcherrima*
Varietal Denomination: Bonpoiakaichi

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 11/590,987

(22) Filed: Nov. 1, 2006

(51) Int. Cl.
*A01H 5/00* (2006.01)

(52) U.S. Cl. ..... Plt./307
(58) Field of Classification Search ..... Plt./307
See application file for complete search history.

*Primary Examiner*—Wendy Haas
(74) *Attorney, Agent, or Firm*—C. A. Whealy

(57) ABSTRACT

A new and distinct cultivar of Poinsettia plant named 'Bonpoiakaichi', characterized by its compact, upright and mounding plant habit; freely branching habit; mid-season flowering response; inflorescences with intense red-colored flower bracts; and excellent post-production longevity.

1 Drawing Sheet

Botanical designation: *Euphorbia pulcherrima.*
Cultivar denomination: 'Bonpoiakaichi'.

BACKGROUND OF THE INVENTION

The present invention relates to a new and distinct cultivar of Poinsettia plant, botanically known as *Euphorbia pulcherrima* Willd., and hereinafter referred to by the name 'Bonpoiakaichi'.

The new Poinsettia a product of a planned breeding program conducted by the Inventor in Cobbitty, New South Wales, Austrialia. The objective of the breeding program is to create new freely branching Poinsettia cultivars with attractive floral bract coloration.

The new Poinsettia originated from a cross-pollination made by the Inventor in January, 1998 of the *Euphorbia pulcherrima* Willd. cultivar Gutbier V-10, disclosed in U.S. Plant Pat. No. 4,235, as the female, or seed, parent, with a proprietary selection of *Euphorbia pulcherrima* Willd. identified as code number 26, not patented, as the male, or pollen, parent. The cultivar Bonpoiakaichi was discovered and selected by the Inventor as a single flowering plant within the progeny of the stated cross-pollination in a controlled environment in Cobbitty, New South Wales, Australia.

Asexual reproduction of the new Poinsettia by terminal vegetative cuttings in a controlled environment in Cobbitty, New South Wales, Austrialia since June, 1999, has shown that the unique features of this new Poinsettia are stable and reproduced true to type in successive generations of asexual reproduction.

SUMMARY OF THE INVENTION

The cultivar Bonpoiakaichi has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bonpoiakaichi'. These characteristics in combination distinguish 'Bonpoiakaichi' as a new and distinct cultivar of Poinsettia:

1. Compact, upright and mounding plant habit.

2. Freely branching habit.
3. Mid-season flowering response.
4. Inflorescences with intense red-colored flower bracts.
5. Excellent post-production longevity.

In side-by-side comparisons conducted in Cobbitty, New South Wales, Australia, plants of the new Poinsettia differed primarily from plants of the female parent, the cultivar Gutbier V-10, in the following characteristics:

1. Plants of the new Poinsettia were more compact than plants of the cultivar Gutbier V-10.
2. Plants of the new Poinsettia had smaller leaves than plants of the cultivar Gutbier V-10.
3. Plants of the new Poinsettia and the cultivar Gutbier V-10 differed in the flower bract coloration.

In side-by-side comparisons conducted in Cobbitty, New South Wales, Austrialia, plants of the new Poinsettia differed from plants of the male parent selection in the following characteristics:

1. Plants of the new Poinsettia were more compact than plants of the male parent selection.
2. Plants of the new Poinsettia had lighter green-colored leaves than plants of the male parent selection.
3. Plants of the new Ponsettia flowered slightly later than plants of the male parent selection.
4. Plants of the new Poinsettia had lighter red-colored flower bracts than plants of the male parent selection.

Plants of the new Ponsettia can be compared to plants of the Poinsettia cultivar 490, disclosed in U.S. Plant Pat. No. 7,825. In side-by-side comparisons conducted in Cobbitty, New South Wales, Australia, plants of the new Poinsettia differed from plants of the cultivar 490 in the following characteristics:

1. Plants of the new Poinsettia were more compact than plants of the cultivar 490.
2. Plants of the new Poinsettia were less vigorous than plants of the cultivar 490.
3. Plants of the new Poinsettia had smaller and lighter green-colored leaves than plants of the cultivar 490.
4. Plants of the new Poinsettia had narrower flower bracts than plants of the cultivar 490.

BRIEF DESCRIPTION OF THE PHOTOGRAPHS

The accompanying photographs illustrate the overall appearance of the new Poinsettia. These photographs shows the colors as true as it is reasonably possible to obtain in colored reproductions of this type. Colors in the photographs may differ slightly from the color values cited in the detailed botanical description which accurately describe the colors of the new Poinsettia.

The photograph at the top of the sheet comprises a side perspective view of a typical flowering plant of 'Bonpoiakaichi' grown in a container.

The photograph at the bottom of the sheet is a close-up view of a typical inflorescence of 'Bonpoiakaichi'.

DETAILED BOTANICAL DESCRIPTION

In the following description, color references are made to The Royal Horticultural Society Colour Chart, 2001 Edition, except where general terms of ordinary dictionary significance are used. The aforementioned photograph and following observations and measurements describe plants grown in Yellow Rock, New South Wales, Australia during the winter in a polyethylene-covered greenhouse and under conditions and practices which approximate those generally used in commercial Poinsettia production. During the production of the plants, day temperatures averaged 28° C. and night temperatures averaged 18° C. Measurements and numerical values represent averages for typical flowering plants. Single plants were grown in 15-cm containers and pinched one time. Plants were about five months old when the photographs and the detailed description were taken.

Botanical classification: *Euphorbia pulcherrima* cultivar Bonpoiakaichi.

Parentage:

*Female, or seed, parent.*—*Euphorbia pulcherrima* Willd. cultivar Gutbier V-10, disclosed in U.S. Plant Pat. No. 4,235.

*Male, or pollen, parent.*—Proprietary selection of *Euphorbia pulcherrima* Willd. identified as code number 26, not patented.

Propagation:

*Type.*—Terminal vegetative cuttings.

*Time to initiate roots.*—About ten days at 20° C. to 25° C.

*Time to produce a rooted young plant.*—About four weeks at 20° C. to 25° C.

*Root description.*—Fine, fibrous, fleshy; light brown to white in color.

*Rooting habit.*—Freely branching; dense.

Plant description:

*Plant habit and form.*—Compact, upright and mounding plant habit; inverted triangle. Inflorescences positioned above the foliar plane. Moderately vigorous growth habit.

*Plant height.*—About 21.6 cm.

*Plant diameter or spread.*—About 31.4 cm.

*Lateral branch description.*—Quantity: Freely branching habit, about eight lateral branches develop after pinching. Length: About 11.3 cm. Diameter: About 4.5 mm. Internode length: About 2 cm. Strength: Strong. Texture: Smooth, glabrous. Color: 146A.

*Foliage description.*—Arrangement: Alternate, simple. Length: About 12.3 cm. Width: About 6.9 cm. Shape: Ovate. Apex: Acute. Base: Obtuse. Margin: Irregular and shallow lobes; dentate. Venation pattern: Pinnate; reticulate. Texture, upper surface: Smooth, glabrous. Texture, lower surface: Pubescent. Color: Developing foliage, upper surface: 143C. Developing foliage, lower surface: 144A. Fully expanded foliage, upper surface: 147A; venation, 46A. Fully expanded foliage, lower surface: 138A; venation, 48A. Petiole: Length: About 3.7 cm. Diameter: About 2 mm. Texture, upper and lower surfaces: Smooth, glabrous. Color, upper and lower surfaces: 46A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter, inflorescence initiation and development is induced under long nyctoperiod conditions. Mid-season flowering, response time is about eight to nine weeks.

*Post-production longevity.*—Excellent post-production longevity; plants of the new Poinsettia maintain good substance and bract color for about two months under interior conditions.

*Inflorescence size.*—Diameter: About 22 cm. Height (depth): About 4 cm.

*Flower bracts.*—Quantity per inflorescence: About ten. Length, largest bracts: About 11.8 cm. Width, largest bracts: About 6.9 cm. Shape: Elliptic. Apex: Acuminate. Base: Truncate to obtuse. Margin: Entire or irregular and shallow lobes. Texture, upper and lower surfaces: Smooth, glabrous; velvety. Venation pattern: Pinnate. Color: Developing or transitional bracts, upper and lower surfaces: 46A. Fully developed bracts, upper and lower surfaces: 45B; venation, 46A. Bract petiole: Length: About 1.7 cm. Diameter: About 2 mm. Texture, upper and lower surfaces: Smooth, glabrous. Color, upper and lower surfaces: Close to 53A.

*Cyathia.*—Quantity per inflorescence: About 18. Diameter of cyathia cluster: About 3.8 cm. Length: About 9 mm. Width: About 7 mm. Shape: Globose. Color, immature: 143B. Color, mature: 143B to 143C. Nectaries: Quantity per cyathium: Typically one. Size: About 4 mm. Color: 3A.

*Peduncles.*—Length: About 3.7 cm. Diameter: About 1 mm. Strength: Strong to moderately strong. Texture: Smooth, glabrous. Color: 145A.

*Reproductive organs.*—Stamens: Quantity per cyathium: About ten. Anther shape: Oval. Anther length: About 0.2 mm. Anther color: 60A. Amount of pollen: Scarce. Pollen color: Close to 9A. Pistils: Quantity per cyathium: One. Pistil length: About 4 mm. Style color: 60A. Stigma shape: Three-parted. Stigma color: 60A. Ovary color: 145A. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 12° C. to about 40° C.

It is claimed:

1. A new and distinct Poinsettia plant named 'Bonpoiakaichi' as illustrated and described.

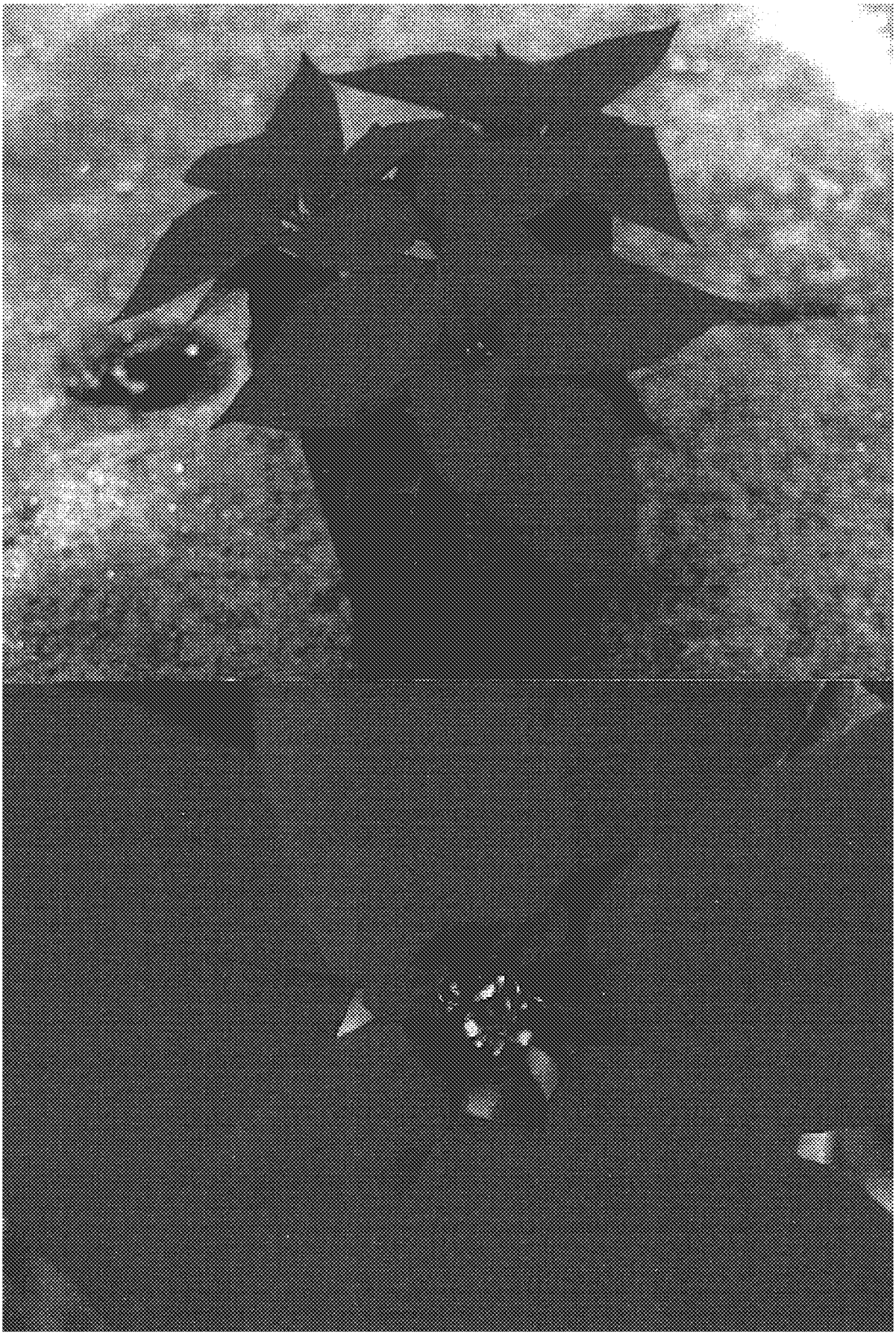

* * * * *